(12) United States Patent
Tepic

(10) Patent No.: US 10,172,631 B2
(45) Date of Patent: Jan. 8, 2019

(54) SURGICAL BONE HOLDING FORCEPS WITH A DRILLING GUIDE

(71) Applicant: KYON AG, Zürich (CH)

(72) Inventor: Slobodan Tepic, Zürich (CH)

(73) Assignee: KYON AG, Zürich (CH)

( * ) Notice: Subject to any disclaimer, the term of this patent is extended or adjusted under 35 U.S.C. 154(b) by 662 days.

(21) Appl. No.: 14/373,048

(22) PCT Filed: Jan. 18, 2013

(86) PCT No.: PCT/EP2013/050939
§ 371 (c)(1),
(2) Date: Jul. 18, 2014

(87) PCT Pub. No.: WO2013/107859
PCT Pub. Date: Jul. 25, 2013

(65) Prior Publication Data
US 2015/0005779 A1    Jan. 1, 2015

(30) Foreign Application Priority Data
Jan. 19, 2012  (EP) ..................... 12151701

(51) Int. Cl.
*A61B 17/58* (2006.01)
*A61B 17/60* (2006.01)
*A61F 2/00* (2006.01)
*A61B 17/17* (2006.01)
*A61B 17/28* (2006.01)

(52) U.S. Cl.
CPC .......... *A61B 17/1714* (2013.01); *A61B 17/28* (2013.01)

(58) Field of Classification Search
CPC . A61B 17/28; A61B 17/2804; A61B 17/2812; A61B 17/2816; A61B 17/282; A61B 17/2833; A61B 17/2841; A61B 17/285; A61B 17/29; A61B 17/295; A61B 17/17; A61B 17/1714; A61B 17/8866
USPC .......................................... 606/96, 207, 324
See application file for complete search history.

(56) References Cited

U.S. PATENT DOCUMENTS

| 2,181,746 | A |   | 11/1939 | Siebrandt |            |
|-----------|---|---|---------|-----------|------------|
| 5,697,933 | A |   | 12/1997 | Gundlapalli |          |
| 5,735,874 | A | * | 4/1998  | Measamer  | A61B 17/2909 |
|           |   |   |         |           | 606/208    |
| 2009/0254130 | A1 |  | 10/2009 | Wotton |            |

FOREIGN PATENT DOCUMENTS

| DE | 87 08 304   U1 |   | 9/1987  |           |
|----|----------------|---|---------|-----------|
| EP | 0813843     A1 |   | 12/1997 |           |
| WO | 2011151654  A1 |   | 12/2011 |           |
| WO | WO 2011151654 A1 | * | 12/2011 | A61B 17/17 |

OTHER PUBLICATIONS

International Search Report cited in PCT/EP2013/050939 dated Apr. 2, 2013, 3 pgs.

* cited by examiner

*Primary Examiner* — Si Ming Ku
(74) *Attorney, Agent, or Firm* — Rothwell, Figg, Ernst & Manbeck, P.C.

(57) ABSTRACT

The invention relates to surgical bone holding forceps provided with a drilling guide that allows for drilling parallel to the pointed jaws of the forceps clamped to a bone. Another aspect of the invention is the friction-based, stepless locking mechanism that retains the forceps arms in position with the jaws clamped to the bone.

14 Claims, 5 Drawing Sheets

SURGICAL BONE HOLDING FORCEPS WITH A DRILLING GUIDE

CROSS REFERENCE TO RELATED APPLICATION

This application is a 35 U.S.C. 371 National Phase Entry Application from PCT/EP2013/050939, filed Jan. 18, 2013, which claims the benefit of European Patent Application No. 12151701.5 filed on Jan. 19, 2012, the disclosure of which is incorporated herein in its entirety by reference.

BACKGROUND

1. Field of the Invention

The invention relates to surgical bone holding forceps provided with a drilling guide that allows for drilling parallel to the pointed jaws of the forceps clamped to a bone. This instrument is of particular usefulness in placing guide wires for bone anchors used in reconstruction or replacement of cruciate ligaments, but also for general orthopedic applications such as insertion of lag screws across a bone fracture, whereby the forceps have a dual function—that of reducing and holding bone fragments in apposition and providing a precise guide for drilling a hole through the bone fragments in very close proximity to the pointed jaws of the forceps.

Another aspect of the invention is the friction-based, stepless locking mechanism that retains the forceps arms in position with the jaws clamped to the bone.

2. Discussion of Related Art

A search by the inventor has uncovered two families of surgical instruments conceptually related to the present invention: (1) so-called C-guides used for drilling holes in usually intact bones; and (2) reduction forceps for drilling holes in fractured bones.

U.S. Pat. No. 1,944,116, by Stratman discloses a friction lever locking mechanism for handles of pliers, pinchers, clamps and the like.

U.S. Pat. No. 2,881,649, by Ball et al. discloses pliers with handle latching means based on a ratcheted hinged plate at the back side of the handles, which is a commonly used mechanism in surgical instruments.

U.S. Pat. No. 4,896,661, by Bogert et al. discloses an orthopedic ratcheting forceps with the ratchet disposed between the handles and the pivot.

U.S. Pat. No. 5,674,244, by Mathys discloses a micro ratcheted locking device on pliers-shaped tool. This mechanism is very complex and prone to damage and wear of the ratchet teeth.

U.S. Pat. No. 2,181,746, by Siebrandt discloses a bone clamp with an adjustable drill guide.

U.S. Pat. No. 4,235,428, by Davis discloses a bone transfixation pin guide—a typical C-guide device.

U.S. Pat. No. 4,312,337, by Donohue discloses circular cannula and drill guide forceps.

U.S. Pat. No. 4,444,180, by Schneider et al. discloses a drill guide intended to guide the drill bit into a specific location in the bone. However, as is the case with many similar devices on the market, this guide works properly for only a single position of the forceps, i.e. for only one size of the bone it is clamped on.

U.S. Pat. No. 5,154,720, by Trott et al. discloses a C-type drill guide with an axially sliding drill sleeve held by a locking mechanism inside the guide tube.

U.S. Pat. No. 5,725,532, by Shoemaker discloses a reduction clamp provided by a drill guide on one of the arms. The drill guidance does not target the opposite tip of the clamp, except, at best, in one position.

U.S. Pat. No. 5,514,144, by Bolton discloses a targeting drill guide for placement of a straight tibio-femoral bone tunnel for ACL reconstruction, basically a C-clamp type device.

U.S. Pat. No. 7,192,432, by Wetzler et al. discloses a surgical drill guide with multiple angular positions for the K-wire sleeve. This is also a C-arm type device primarily intended for preparing tibia bone tunnels in ACL reconstruction.

SUMMARY OF THE INVENTION

According to one aspect of the invention, scissors-shaped forceps are provided by a guide shaft mounted between the jaws or the arms of the forceps by means of pivots so that the line connecting the pivots is parallel to the line connecting the clamping tips of the forceps. This shaft is then used to guide a hinged drill guide freely sliding and rotating on the shaft and provided with a bore for the guide pin, or the drill to be drilled into the bone. The pivots that connect the guide shaft to the arms of the forceps can be placed on either side of the master pivot—for higher precision distally, closer to the bone, or should the precision be of lesser interest than space, proximally, away from the bone. Hinged drill guides with different bore diameters are provided to accommodate a selection of guide pins, K-wires (short for Kirschner wires) and drills.

According to another aspect of the invention, the forceps are provided with different style tips of the jaws aiding in placement of the entry and/or exit holes for different applications. The simplest and most useful tips are pointed style, with a preferred modification of a V-groove nose on the entry side to keep the guide wire centered over the pointed tip.

According to another aspect of the invention, a friction-based locking mechanism is provided to maintain the position of the arms of the forceps with the tips of the jaws closed on the bone. The locking mechanism preferably comprises two main components: (1) an arch-shaped friction bar with its center of curvature coincident with the axis of the master pivot; and (2) a brake lever provided by a gliding hole for the friction bar and pivoted to a forceps arm at a distance from the gliding hole to guarantee friction locking of the two components opposing the opening movement of the forceps arms. The brake lever is held engaged with the friction bar by a brake spring. Release of the brake is accomplished by unloading of the locking mechanism by pressing the forceps further towards closed position, and then releasing the brake by a finger action opposite to the brake spring.

The materials used to produce the forceps are either surgical stainless steels, hardened as appropriate, or titanium alloys such as TiAl6V4.

DETAILED DISCLOSURE

Figure 1:
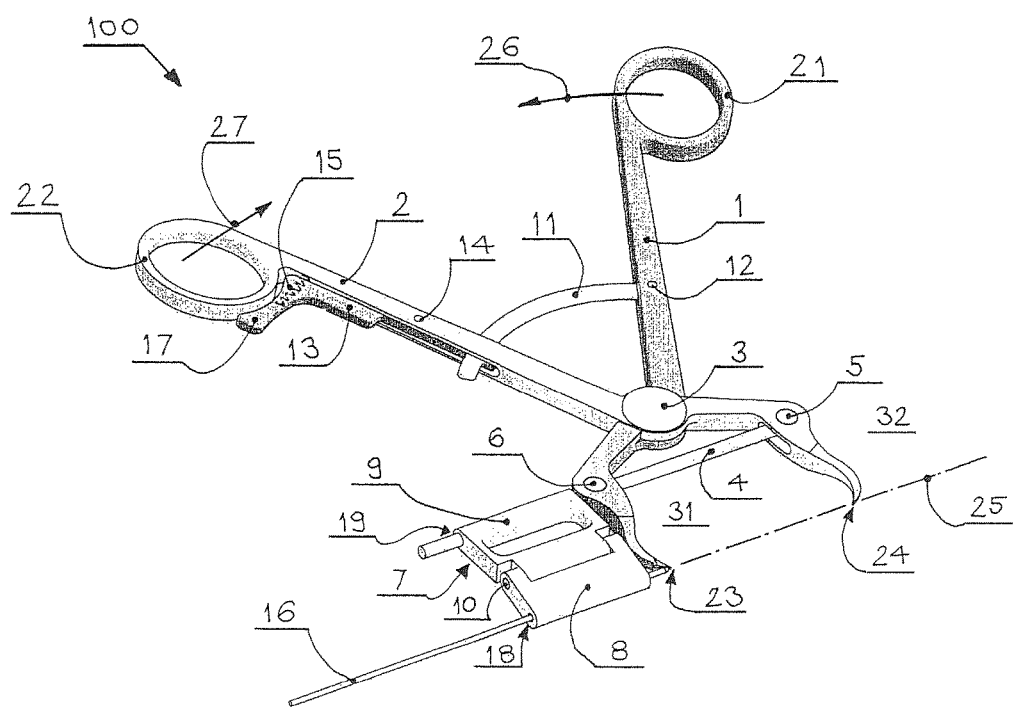
FIG. 1 is a perspective view of the forceps according to the present invention.

FIG. 1 shows a bone forceps 100 according to the present invention. The forceps are comprised of two nearly identically shaped forceps arms 1 and 2, connected by a master pivot 3. Distal ends of the forceps arms 1 and 2 function as jaws, 31 and 32 respectively, with the pointed tips 23 and 24. At the proximal ends the arms are provided by finger grips 21 and 22. Distally to the master pivot 3 a guide shaft 4 is connected to the jaws of the forceps via pivots 5 and 6. The guide shaft 4 is welded to the pivot 5 while it freely glides through the hole in the pivot 6. For all positions of the forceps the guide shaft 4 is parallel to the line 25 connecting the pointed tips 23 and 24 of the forceps.

A hinged drill guide 7 comprises an element 9 with a bore 19 that can slide and rotate on the guide shaft 4, hinged via a pin 10 to the drill guide element 8. The drill guide element 8 is provided by a bore 18 for the guide pin 16. Alternatively, drill bits or K-wires can also be guided by different hinged guides 7 with appropriate diameters of the bore 18.

Proximally to the master pivot 3, a friction bar 11 is attached to the arm 1 via a pivot 12. The friction bar is arch-shaped with the center of the curvature at the axis of the master pivot 3. The friction bar passes through the brake lever 13, attached to the arm 2 via pivot 14. A brake spring 15 maintains the brake lever 13 engaged against the friction bar 11, preventing the opening of the forceps arms. The arms of the forceps can always be moved towards each other as shown by arrows 26 and 27. In normal use the thumb is to be passed through the finger grip 21; the middle finger through the finger grip 22, leaving the index finger free to act on the brake release 17 of the brake lever 13. Pulling the brake release 17 towards the finger grip 22, will compress the spring 15 and disengage the brake lever 13 from the friction bar 11 to allow the forceps arms to be moved apart.

Figure 2:
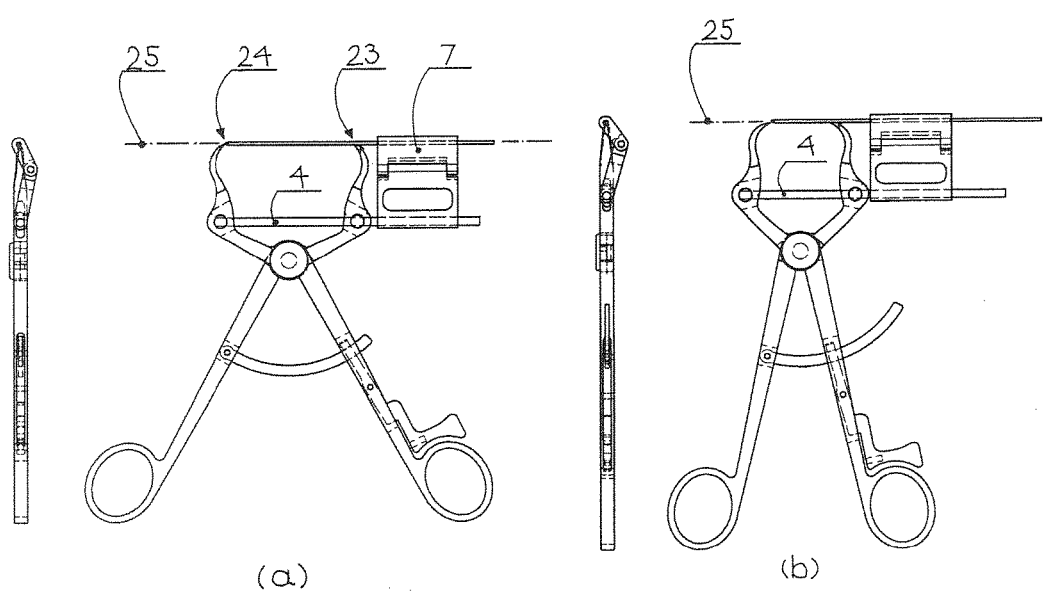
FIG. 2 is a schematic view of the forceps in the fully open and in a half-closed position, demonstrating the parallelism of the hinged drill guide and the line connecting the pointed tips of the forceps.

FIG. 2a illustrates the forceps in the open position. The guide shaft 4 is parallel to the line 25 connecting the pointed tips 23 and 24 of the forceps. The hinged drill guide 7 is almost fully extended, as shown on the side view, to bridge the distance from the guide shaft 4 to the line 25.

FIG. 2b illustrates the forceps in the half closed position. The guide shaft 4 remains parallel to the line 25 connecting the pointed tips 23 and 24 of the forceps. The hinged drill guide 7 is now somewhat flexed, as shown on the side view, to adjust to the distance from the guide shaft 4 to the line 25. Drilling of the hole does not have to be at the very proximity to the tips of the forceps—hinged guide 7 can be moved and adjusted to an entry hole in the bone within a range of several millimeters—the drilled hole, however, will always remain parallel to the line 25. For example, two parallel K-wires can be driven into bone fragments held together by the forceps, as is usually required to prevent rotation.

Figure 3:
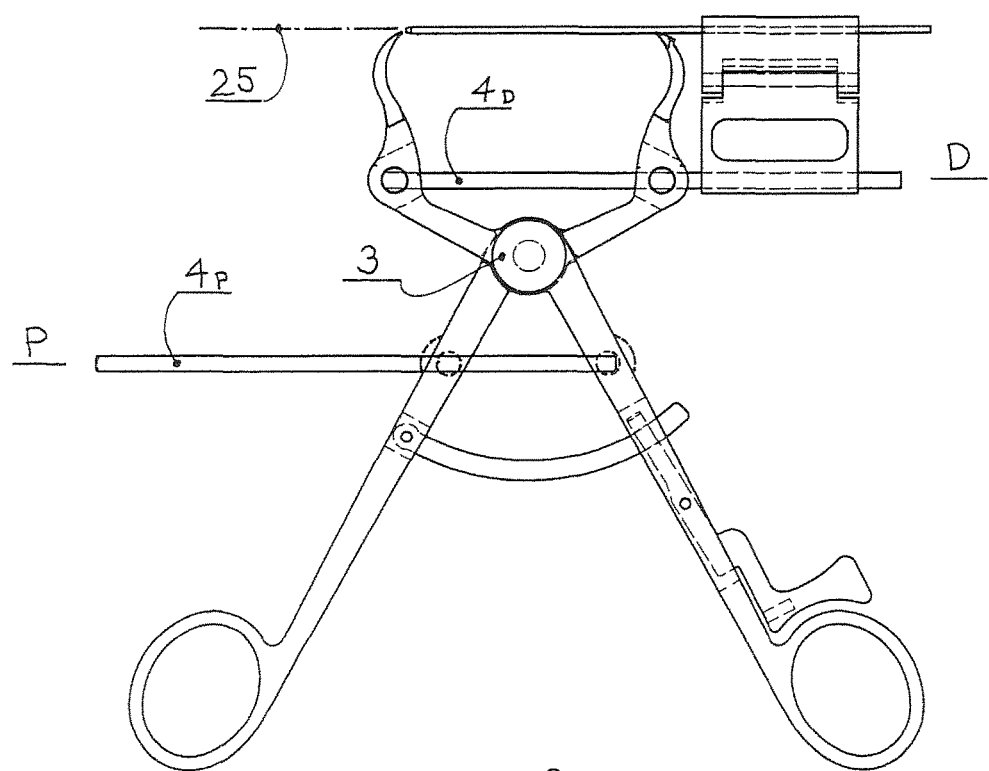
FIG. 3 shows alternative positions of the guide shaft distally or proximally to the master pivot.

FIG. 3 shows a possibility to place the guide shaft 4 either distally, marked by D, or proximally, marked by P, to the master pivot 3.

Figure 4:
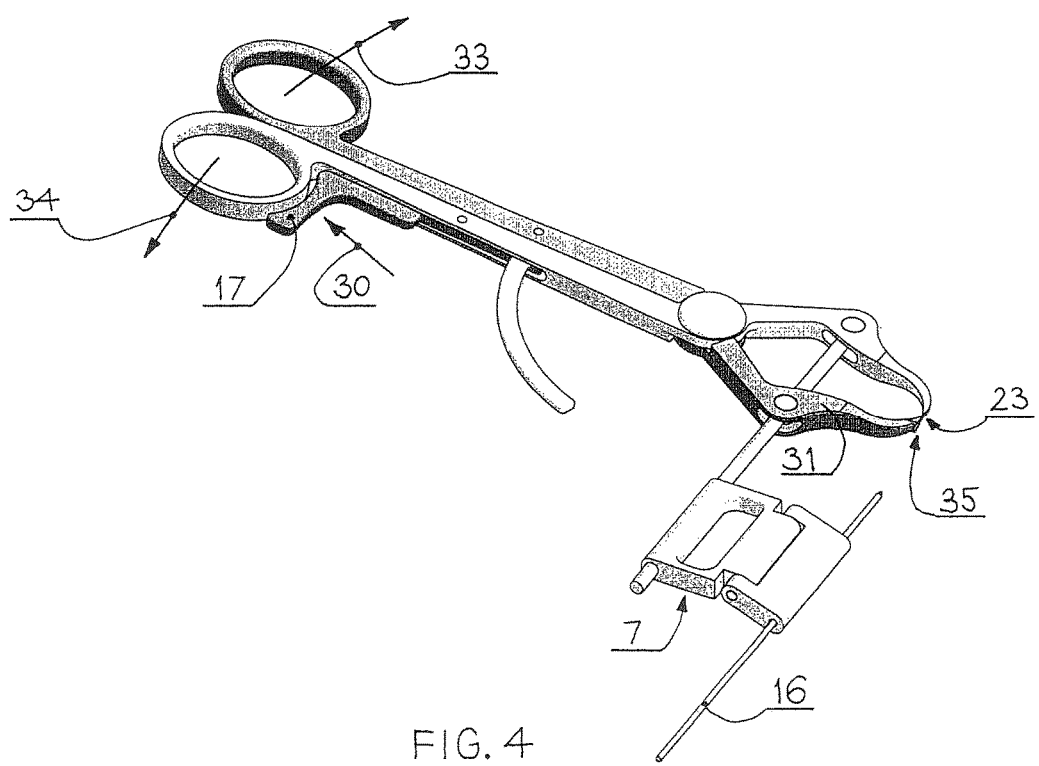
FIG. 4 is a perspective view of the forceps according to the present invention in the closed position.

FIG. 4 shows the forceps in fully closed position. To open the forceps, as shown by arrows 33 and 34, requires the brake release 17 to be pushed towards the finger grips, as shown by arrow 30. A V-shaped nose 35 at the tip of the jaw 31 can be of help in centering the guide pin 16 over the pointed tip 23 during drilling.

Figure 5:
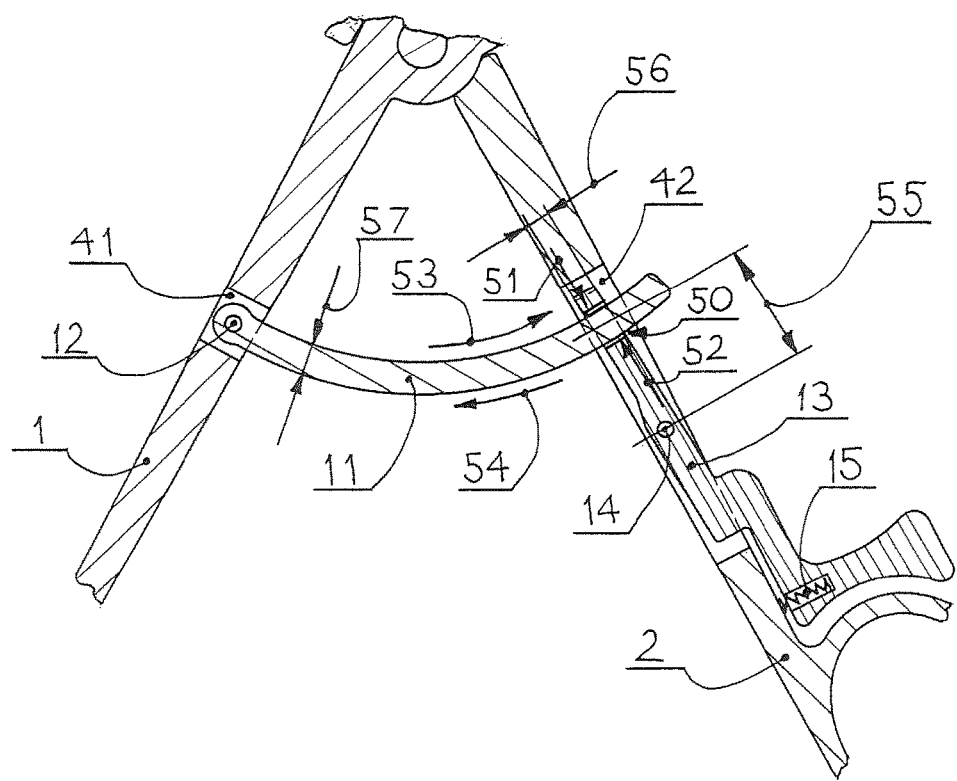
FIG. 5 is a partial cross sectional view of the friction brake components.

FIG. 5 illustrates the main components of the friction brake mechanism. The friction bar 11 is attached to the forceps arm 1 within the slot 41 via pivot 12. The brake lever 13 is attached to the forceps arm 2 within the slot 42 via pivot 14. The spring 15 pushes the brake lever 13 at its distal end away from the forceps arm 2. This brings the friction bar 11 and the brake lever 13 into contact at opposite points within the slot 50 in the brake lever 13, creating normal pressure indicated by arrows 51 and 52. The width of the slot 50 is slightly larger than the width of the friction bar. The friction bar can glide through the slot 50 in the direction of the arrow 53 (closing of the forceps), but is prevented from gliding in the direction 54 (opening of the forceps) as long as the distance 55 is larger than the width 56 of the brake lever 13 divided by 2 times the coefficient of friction. A safe function with hardened stainless steel used for both components is obtained by making the distance 55 about factor 5 to 10 larger than the width 56. The dimension 57 of the friction bar plays only a second order effect.

Hardened surgical stainless steel is the preferred choice for most of the forceps components. Reducing friction in all pivots is desired for a smooth operation. Tight tolerances with minimal play will increase the precision of the drill guide. Anti friction coatings, such as Amorphous Diamond-Like Coating (ADLC) can be of good use on e.g. guide shaft 4 and the master pivot 3.

An important advantage of the disclosed instrument over many types of C-guides, is a single hand use of the device when being clamped to the bone. Visualization is unimpeded and the instrument can be manufactured with extremely fine tactile feedback, being free of any ratcheting in its locking mechanism. Use is particularly targeted to arthroscopic procedures in the joints, e.g. insertion of the bone anchors or preparation of the bone tunnels for Anterior Cruciate Ligament (ACL) replacement, whereby the pointed tip 24 is placed inside the joint at the desired location, which is either the origin or the insertion of the ACL, and the pointed tip 23 and the drill guide mechanism are placed on the outside surface of either the femur or the tibia. Following insertion of the guide pin and verification of its exit position at the targeted, intra-articular location, a cannulated drill is used over the guide pin from outside-in to drill the hole of the appropriate diameter for the anchor or the bone tunnel.

It will be clear to those skilled in art that minor modifications of the disclosed examples can lead to particular solutions, which can have further advantages. For example, different tips of the jaws can be made for different uses; a conventional drill sleeve can be used between the drill guide 7 and the bone; forceps jaws can be bent out of the plane of the forceps arms; several sizes can be produced for different bones; the forceps need not be symmetric as shown here; finger grips can be replaced by hand grips pushed apart by a spring; titanium alloys can be used for very small bones. Friction brake can be used on forceps without the drill guide function and conversely, the drill guide can be used on forceps with conventional locking mechanisms.

The invention discloses forceps, preferably, but not limited to, surgical bone forceps, provided by a mechanism that allows for drilling holes directed in parallel to the line connecting the tips of the forceps in all positions of the forceps, i.e. independently of the size of the bone the forceps are clamped onto. Disclosed is also a reliable, robust friction brake that holds the forceps in the closed position.

The invention claimed is:

1. A bone holding forceps comprising jaws with clamping tips and a first arm and a second arm which can be moved toward each other, wherein the forceps are provided with a drilling guide, wherein the drilling guide allows for drilling parallel to a line connecting the clamping tips of the jaws, wherein the drilling guide is guided on a guiding shaft mounted between the jaws or the first and second arms by means of pivots, so that a line connecting the pivots is parallel to the line connecting the clamping tips of the jaws, and wherein the guiding shaft is fixed to a pivot which is connected to said first arm and freely glides through a hole in a pivot connected to said second arm.

2. The bone holding forceps of claim 1, wherein the guiding shaft is adapted for guiding the drilling guide freely slidable and rotating on the guiding shaft, wherein the drilling guide is provided with a bore for a guide pin, a guide wire or a drill to be drilled into the bone.

3. The bone holding forceps according to claim 2, wherein the drilling guide is hinged.

4. The bone holding forceps of claim 1, which has pointed jaw tips.

5. The bone holding forceps according to claim 4, wherein said pointed jaw tips have a V-groove nose on the pointed jaw tip closest to said drilling guide.

6. The bone drilling forceps according to claim 1 which has a master pivot with an axis and a friction-based stepless locking mechanism for retaining the forceps arms in position when the jaws are configured to be clamped to the bone.

7. The bone holding forceps according to claim 6, wherein the locking mechanism comprises a curved, arch-shaped friction bar attached to said first arm of the forceps with its center of curvature coincident with the axis at the master pivot of the forceps, a gliding hole for the friction bar in the second arm of the forceps, and a brake lever attached to the second arm at a distance from the gliding hole to provide friction locking of the friction bar.

8. A bone holding forceps comprising jaws with clamping tips and arms, wherein said bone holding forceps comprises a drilling guide and wherein the drilling guide allows for drilling parallel to a line connecting the clamping tips of the jaws, wherein the drilling guide comprises an element with a bore that can slide and rotate on a guiding shaft mounted between the jaws or the arms by means of pivots, so that a line connecting the pivots is parallel to the line connecting the clamping tips of the jaws, and wherein the guiding shaft is fixed to a pivot which is connected to said first arm and freely glides through a hole in a pivot connected to said second arm.

9. The bone holding forceps according to claim 8, wherein the guiding shaft is adapted for guiding the drilling guide freely slidable and rotating on the guiding shaft, wherein the drilling guide is provided with another bore for a guide pin, a guide wire or a drill to be drilled into the bone.

10. The bone holding forceps according to claim 8, which has pointed jaw tips.

11. The bone holding forceps according to claim 10, wherein said pointed jaw tips have a V-groove nose on the pointed jaw tip closest to said drilling guide.

12. The bone holding forceps according to claim 8, which has a friction-based stepless locking mechanism for retaining the forceps arms in position when the jaws are clamped to the bone.

13. The bone holding forceps according to claim 12, wherein the locking mechanism comprises a curved friction bar attached to a first arm of the forceps with its center of curvature coincident with the axis at the master pivot of the forceps, a gliding hole for the friction bar in the second arm of the forceps, and a brake lever attached to the second arm at a distance from the gliding hole to provide friction locking of the friction bar.

14. The bone holding forceps according to claim 13, wherein the curved friction bar is an arch shaped friction bar.

* * * * *